US012108981B2

(12) United States Patent
Otsubo

(10) Patent No.: US 12,108,981 B2
(45) Date of Patent: Oct. 8, 2024

(54) MEDICAL DEVICE

(71) Applicant: TERUMO KABUSHIKI KAISHA, Tokyo (JP)

(72) Inventor: Seiichi Otsubo, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 808 days.

(21) Appl. No.: 17/023,584

(22) Filed: Sep. 17, 2020

(65) Prior Publication Data

US 2021/0000538 A1 Jan. 7, 2021

Related U.S. Application Data

(63) Continuation of application No. PCT/JP2019/009729, filed on Mar. 11, 2019.

(30) Foreign Application Priority Data

Mar. 20, 2018 (JP) ................................. 2018-052243

(51) Int. Cl.
*A61B 18/14* (2006.01)
*A61B 17/00* (2006.01)
(Continued)

(52) U.S. Cl.
CPC .......... *A61B 18/1492* (2013.01); *A61M 29/00* (2013.01); *A61B 2017/00247* (2013.01);
(Continued)

(58) Field of Classification Search
CPC ...... A61B 18/1492; A61B 2017/00247; A61B 2017/00867; A61B 2018/0038;
(Continued)

(56) References Cited

U.S. PATENT DOCUMENTS 5,221,281 A 6/1993 Klicek
8,679,107 B2 * 3/2014 Mirza ................ A61B 18/1482
606/41

(Continued)

FOREIGN PATENT DOCUMENTS

JP 2554849 B2 11/1996
JP 2015518741 A 7/2015
(Continued)

OTHER PUBLICATIONS

The European Search Report (under R. 61 or R. 63 EPC) or the Supplementary European Search Report (Art. 153(7) EPC) issued Mar. 30, 2021, by the European Patent Office in corresponding European Patent Application No. 19772141.8-1122. (4 pages).
(Continued)

*Primary Examiner* — Linda C Dvorak
*Assistant Examiner* — Abigail Bock
(74) *Attorney, Agent, or Firm* — Buchanan Ingersoll & Rooney PC

(57) ABSTRACT

A medical device that has high pushing performance is capable of forming a hole in a biological tissue in a living body, is capable of being arbitrarily shaped, and is capable of suppressing a kink. The medical device may be used to form a hole in an oval fossa in a living body. The medical device includes: a hollow dilator made of resin; a core made of metal that is disposed in a part in a circumferential direction of the dilator and extends in a long axis direction of the dilator; and an output unit that is disposed in a distal portion of the dilator and outputs energy to form the hole in the oval fossa, in which the core is embedded in between an inner peripheral surface and an outer peripheral surface of the dilator, and the core has conductivity and is electrically connected to the output unit.

21 Claims, 6 Drawing Sheets

(51) Int. Cl.
*A61B 18/00* (2006.01)
*A61M 29/00* (2006.01)

(52) U.S. Cl.
CPC .............. *A61B 2017/00867* (2013.01); *A61B 2018/0038* (2013.01); *A61B 2018/00577* (2013.01); *A61B 2018/00595* (2013.01)

(58) Field of Classification Search
CPC ........... A61B 2018/00577; A61B 2018/00595; A61M 29/00
See application file for complete search history.

(56) References Cited

U.S. PATENT DOCUMENTS

| | | | | |
|---|---|---|---|---|
| 2006/0241366 | A1* | 10/2006 | Falwell | A61B 5/6856 606/41 |
| 2014/0236125 | A1* | 8/2014 | Watanabe | A61M 25/09033 604/528 |
| 2015/0134047 | A1* | 5/2015 | McClain | A61L 31/10 623/1.42 |
| 2015/0374431 | A1* | 12/2015 | Davies | A61B 18/1477 606/41 |
| 2016/0242661 | A1* | 8/2016 | Fischell | A61B 5/6852 |
| 2019/0216503 | A1 | 7/2019 | Otsubo | |

FOREIGN PATENT DOCUMENTS

| | | |
|---|---|---|
| JP | 2016-513520 A | 5/2016 |
| JP | 2017512569 A | 5/2017 |
| WO | 2018047901 A1 | 3/2018 |
| WO | 2018/062387 A1 | 4/2018 |

OTHER PUBLICATIONS

Office Action (Communication pursuant to Article 94(3) EPC) issued Apr. 13, 2021, by the European Patent Office in corresponding European Patent Application No. 19 772 141.8-1122. (5 pages).
An English Translation of the International Search Report (Form PCT/ISA/210) and the Written Opinion of the International Searching Authority (Form PCT/ISA/237) issued on Jun. 4, 2019, by the Japanese Patent Office in corresponding International Application No. PCT/JP2019/009729. (5 pages).
Office Action (Notice of Reasons for Refusal) issued Sep. 5, 2022, by the Japan Patent Office in corresponding Japanese Patent Application No. 2020-508229 and an English Translation of the Office Action. (6 pages).
International Search Report (PCT/ISA/210) issued on Jun. 4, 2019, by the Japan Patent Office as the International Searching Authority for International Application No. PCT/JP2019/009729.
Written Opinion (PCT/ISA/237) issued on Jun. 4, 2019, by the Japan Patent Office as the International Searching Authority for International Application No. PCT/JP2019/009729.

* cited by examiner

MEDICAL DEVICE

CROSS-REFERENCES TO RELATED APPLICATIONS

This application is a continuation of International Application No. PCT/JP2019/009729 filed on Mar. 11, 2019, which claims priority to Japanese Patent Application No. 2018-052243 filed on Mar. 20, 2020, the entire content of both of which is incorporated herein by reference.

FIELD OF THE INVENTION

This disclosure generally relates to a medical device for forming a hole in biological tissue in a living body and a method for forming a hole in biological tissue.

BACKGROUND DISCUSSION

A heart repeatedly contracts and expands at suitable timing by a current flowing through a cardiac muscle tissue called a conducting system of the heart (cardiac conducting system), thereby circulating blood. When the generation and the transmission of electric signals flowing through the conducting system of the heart become less normal, the contraction and the expansion become impossible at the suitable timing, thus causing an arrhythmia.

One known method for treating arrhythmia involves interrupting a conduct path of signals that cause the arrhythmia by heating or cooling ablation. In order to perform this treatment method, an ablation device that is percutaneously inserted to a left atrium, and is capable of performing the ablation of a conduct path of signals that is positioned in the left atrium has been known. Such an ablation device is frequently used because the ablation device is minimally invasive and can obtain a high effect.

In order to perform the ablation in the left atrium, a procedure called the Brockenbrough method in which a needle is inserted from a right atrium to a thin partition wall called an oval fossa in the atrial septum to create a hole that leads from the right atrium to the left atrium becomes necessary. A transseptal needle that is a device for performing the abovementioned Brockenbrough method includes a mechanical needle and a radio frequency needle. The radio frequency needle forms a hole in the atrial septum by heating and modifying the biological tissue with an electrode that outputs the high frequency energy.

The transseptal needle is generally provided with a metal tube. Therefore, the transseptal needle has high pushing performance for forming a hole in biological tissue. In addition, the transseptal needle is provided with the metal tube, so that an operator can arbitrarily bend and use the transseptal needle in accordance with an anatomical condition of a patient. For example, U.S. Pat. No. 8,679,107 describes a transseptal needle in which a metal tube is disposed inward of a tube made of resin.

SUMMARY

The metal tube is bent to cause opposing inner peripheral surfaces to be crushed so as be close to each other, and thus is likely to be kinked. The transseptal needle is provided with the metal tube, and thus is kinked in some cases. When the transseptal needle is kinked, a guide wire or a contrast agent is unable to pass through the inside of the transseptal needle. In addition, if the transseptal needle is kinked, it is difficult to insert the transseptal needle into the sheath.

Disclosed here is a medical device that has high pushing performance capable of forming a hole in a biological tissue in a living body, is capable of being shaped as desired, and is capable of suppressing a kink.

A medical device for forming a hole in a biological tissue in a living body includes: a core made of metal that is disposed in a part of a circumferential direction of the elongated body, and extends in a long axis direction of the elongated body; and an output unit that is disposed in a distal portion of the elongated body, and outputs energy to form the hole in the biological tissue, in which the core is embedded in between an inner peripheral surface and an outer peripheral surface of the elongated body, wherein the core has conductivity, and is electrically connected to the output unit.

According to another aspect, a medical device for forming a hole in biological tissue in a living body comprises: an elongated body made of resin, wherein the elongated body possesses a distal portion and a proximal portion that are spaced apart in an axial direction of the elongated body, the distal portion of the elongated body terminates at a distal end of the elongated body and the proximal portion of the elongated body terminates at a proximal end of the elongated body, the distal portion of the elongated body possesses an outer diameter that decreases in a direction toward the distal end of the elongated body, the elongated body includes a lumen that extends between the proximal and distal portions of the elongated body, the lumen communicates outside the elongated body at both the proximal portion of the elongated body and the distal portion of the elongated body, the lumen in the elongated body is surrounded by an inner peripheral surface of the elongated body, and the elongated body also possesses an outer peripheral surface; a core configured to be connected to an external power supply that supplies current, the core being made of a conductive metal that conducts the current supplied by the external power supply device when the core is connected to the external power supply, wherein the core is completely embedded in the resin from which the elongated body is made so that the entirety of the outer periphery of the core is covered by the resin from which the elongated body is made, the core extends in the axial direction of the elongated body between the proximal portion of the elongated body and the distal portion of the elongated body, the core is made of metal having a circumferential extent, when viewed in a cross-section perpendicular to the central axis of the elongated body, that is less than 360 degrees; and an electrode positioned at the distal portion of the elongated body. The electrode possesses an outer surface that is exposed so that the outer surface of the electrode is contactable with the biological tissue in the living body, with the electrode being electrically connected to the core so that current conducted by the core when the core is connected to the external power supply is supplied to the electrode to form the hole in the biological tissue in the living body.

According to another aspect, a method comprises introducing a portion of a medical device into a living body, wherein the medical device comprises: a hollow elongated body made of resin and possessing distal and proximal portions that are spaced apart in an axial direction of the hollow elongated body; a core made of conductive metal, with the core extending in the axial direction of the hollow elongated body and being embedded in the resin from which the hollow elongated body is made, the core made of metal having a circumferential extent less than 360 degrees relative to the hollow elongated body; and an electrode disposed at the distal portion of the hollow elongated body and electrically connected to the core. The method also includes moving the electrode at the distal portion of the hollow elongated body into contact with biological tissue in the living body; applying energy to the core made of the conductive metal so that the energy is conducted to the electrode; and the energy supplied to the electrode and the contact of the electrode with the biological tissue in the living body causing the biological tissue that is in contact with the electrode to cauterize the biological tissue in the living body and produce a through hole in the biological tissue in the living body.

The core made of metal is disposed in the elongated body made of resin, so that the medical device configured as the above has high pushing performance that allows a hole to be formed in the biological tissue and is capable of being arbitrarily shaped. Moreover, the core made of metal is partially disposed in the circumferential direction of the elongated body made of resin, so that the medical device can suppress a kink from occurring.

BRIEF DESCRIPTION OF THE DRAWINGS

FIG. 6(A) illustrates a state where the medical device is inserted into a right atrium; FIG. 6(B) illustrates a state where the medical device is positioned relative to an oval fossa; FIG. 6(C) illustrates a state where the oval fossa is punctured by the medical device; and FIG. 6(D) illustrates a state where the medical device is pulled out from the sheath.

FIG. 8(A) illustrates a first modification example; and FIG. 8(B) illustrates a second modification example.

DETAILED DESCRIPTION

Set forth below with reference to the accompanying drawings is a detailed description of embodiments of a medical device and method for forming a hole in biological tissue representing examples of the inventive medical device and method disclosed here. The dimensions or scales on the drawings may be exaggerated or different from actuality/reality for convenience of description and illustration. In the present description, a side or end of a device to be inserted into a blood vessel is referred to a "distal side" or "distal end", and a hand-side where the device is operated is referred to as a "proximal side" or "proximal end".

Figure 1:
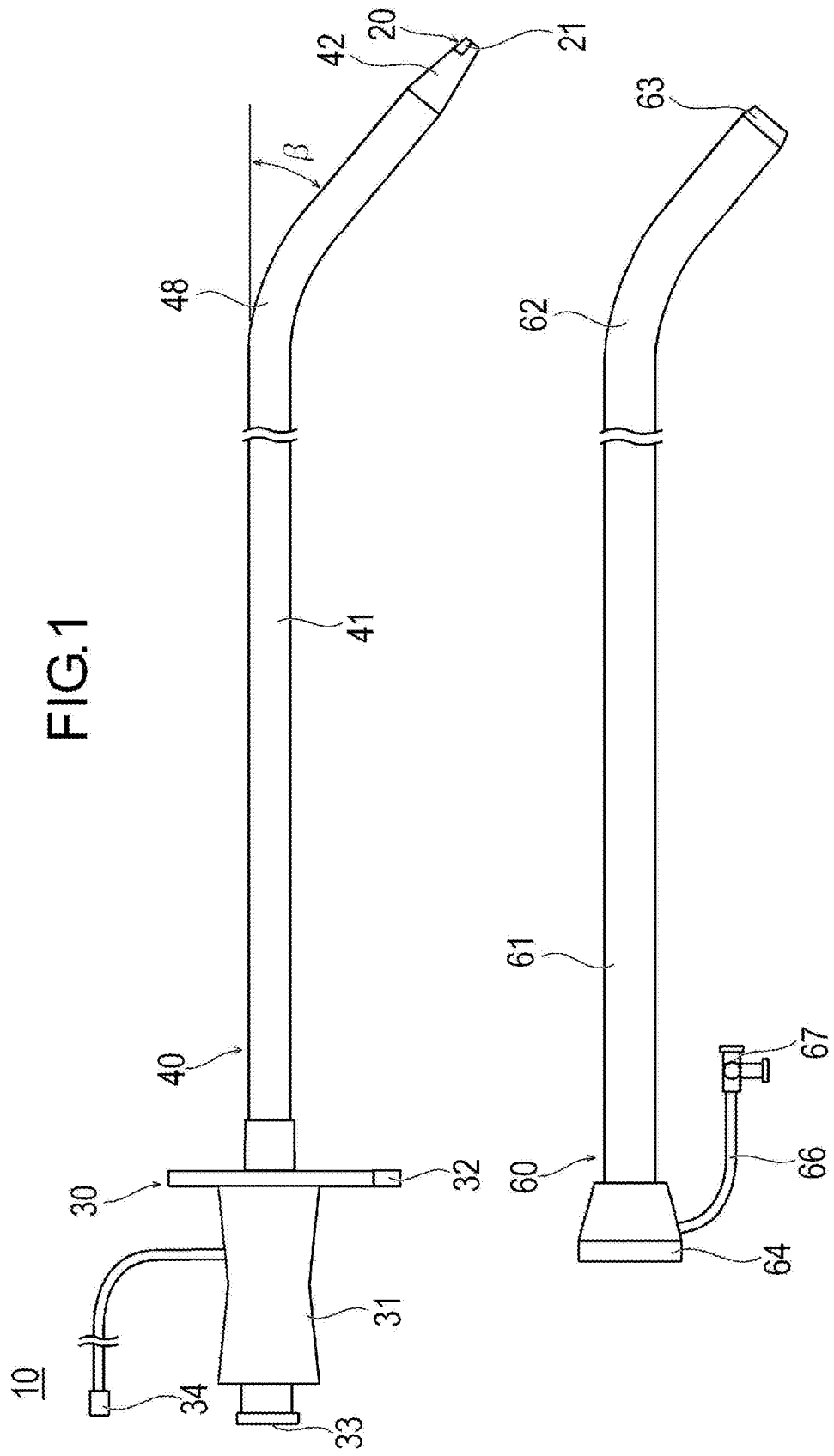
FIG. 1 is a plan view illustrating a medical device and a sheath according to an embodiment.
Figure 2:
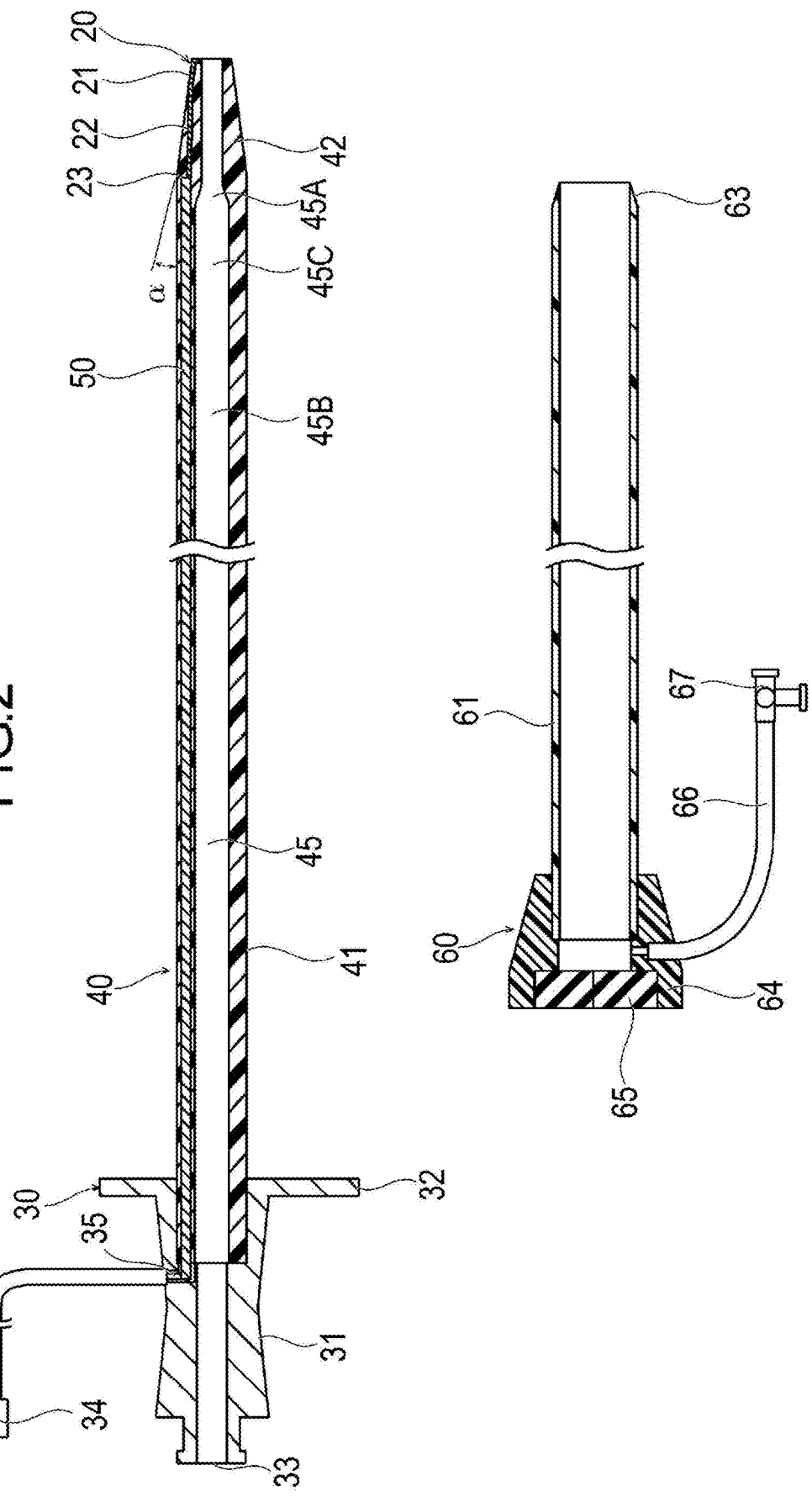
FIG. 2 is a cross-sectional view illustrating the medical device and the sheath.
Figure 3:
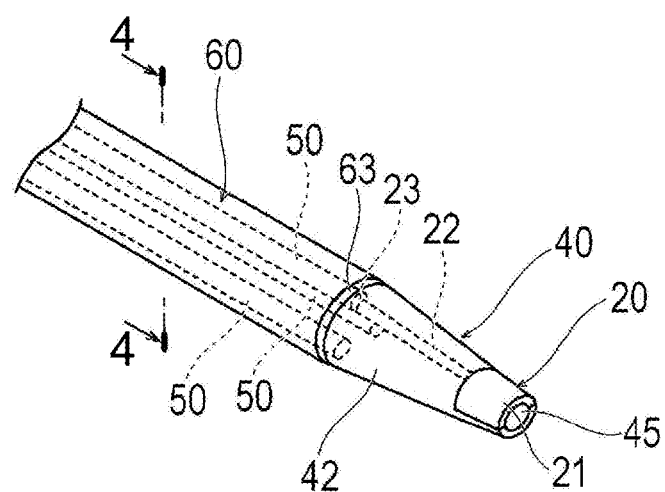
FIG. 3 is a perspective view illustrating a distal portion of the medical device.
Figure 4:
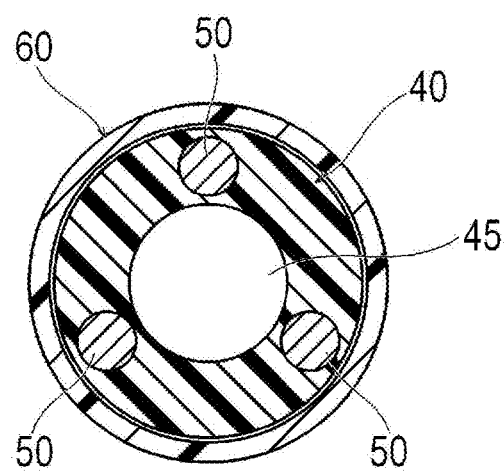
FIG. 4 is a cross-sectional view along a section line 4-4 in FIG. 3.
Figure 5:
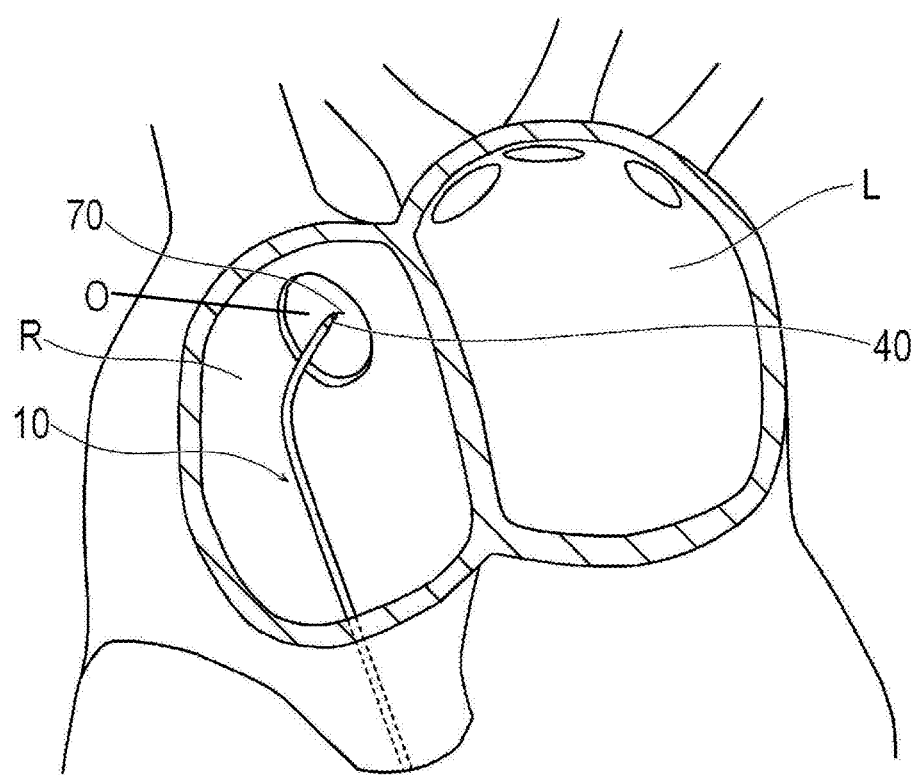
FIG. 5 is a partial cross-sectional view illustrating the inside of a heart.

A medical device 10 in the embodiment according to this disclosure is used for forming a hole in an oval fossa O (an example of biological tissue) in an atrial septum from a right atrium R, and providing an access route that leads from the right atrium R to a left atrium L (see FIG. 5). When there is the access route in the oval fossa O, after a plurality of treatment devices having been percutaneously inserted into the vein, the treatment devices are guided to the right atrium R, and then can be easily inserted into the left atrium. Examples of the treatment devices include an ablation catheter, a ring catheter, and the like. In addition, the medical device 10 also functions as a dilator that expands a hole formed in the oval fossa O. In other words, the medical device 10 is a dilator having a puncture function.

The medical device 10 according to the present embodiment may be used together with a sheath 60, as illustrated in FIGS. 1 to 4. The medical device 10 includes a dilator 40 (elongated body), a core 50, a hole formation unit 20, and an operation unit 30.

The dilator 40 is an elongated tubular body made of resin. The dilator 40 includes a shaft part 41, and a tapered part 42 that is positioned at a distal side of the shaft part 41. In addition, the dilator 40 includes a lumen 45 that penetrates from a distal end to a proximal end so that the lumen 45 is open at opposite (proximal and distal) ends. The shaft part 41 is a tubular body having an approximately constant outer diameter. The outer diameter of the shaft part 41 may gradually decrease toward the distal side. The tapered part 42 includes an outer diameter that decreases in a tapered shape toward a distal side or in the distal direction. An inclination angle α (see FIG. 2) relative to a the central axis of the outer peripheral surface of the tapered part 42 is set as appropriate, and is, for example, 1 to 80 degrees, more preferably 1 to 30 degrees, and further preferably 1 to 10 degrees.

The lumen 45 is positioned at a central portion of the dilator 40 in a cross-section that is vertical to (perpendicular to) the center axis of the dilator 40. That is, when viewing a cross-section of the dilator 40 in a plane perpendicular to the center axis of the dilator 40, the lumen 45 is centrally positioned in the cross-section. The lumen 45 penetrates through or extends throughout the dilator 40 in an axial direction. The lumen 45 is opened at a distal end of the tapered part 42 where the diameter is reduced to minimum. The lumen 45 is configured to accommodate a guide wire. Moreover, a contrast agent or the like can pass through the lumen 45.

The lumen 45 is comprised of a distal side lumen 45A, a proximal side lumen 45B, and a central lumen 45C positioned between the distal side lumen 45A and the proximal side lumen 45B. The proximal side lumen 45B has an inner diameter larger than that of the distal side lumen 45A. The central lumen 45C has an inner diameter that is changed between the distal side lumen 45A and the proximal side lumen 45B. The inner diameter of the proximal side lumen 45B is sufficiently larger than the outer diameter of the guide wire to be inserted. This allows the guide wire to be inserted into the proximal side lumen 45B to smoothly move along an inner peripheral surface of the dilator 40. The central lumen 45C smoothly guides the guide wire passing through the proximal side lumen 45B to the distal side lumen 45A. An inner peripheral surface of the distal side lumen 45A allows the guide wire to slide while coming into contact with the inner peripheral surface with a small clearance.

The dilator 40 includes a shaft bend 48 (bent portion) that is bent at a prescribed angle in a natural state where no external force acts. That is, the shaft bend exist when no force is applied to the dilator 40. The shaft bend 48 is located at a distal portion of the dilator 40. The shaft bend 48 plays a role in causing the distal portion of the dilator 40 to be directed toward the oval fossa O.

The length of the dilator 40 in the axial direction is set as appropriate, and may be, for example, 500 to 800 mm. The outer diameter of the dilator 40 is not particularly limited, and may be, for example, 1.0 to 10.0 mm, preferably 1.5 to 5.0 mm, and more preferably 2.0 to 3.5 mm. The inner diameter of the distal side lumen 45A is not particularly limited, and may be, for example, 0.3 to 5.0 mm, preferably 0.5 to 2.0 mm, and more preferably 0.5 to 1.5 mm. The inner diameter of the proximal side lumen 45B is set as appropriate, and may be, for example, 0.3 to 4.5 mm, preferably 0.5 to 3.0 mm, and more preferably 0.6 to 2.0 mm. An angle β (see FIG. 1) of the shaft bend 48 relative to a proximal portion of the dilator 40 (central axis of the proximal portion of the dilator 40) is not specifically limited, and may be, for example, 10 to 90 degrees, more preferably 30 to 80 degrees, and further preferably 40 to 70 degrees. The angle β can be changed by the operator in accordance with, for example, an anatomical condition of a patient. The length from a distal side end portion of the dilator 40 to the shaft bend 48 is not particularly limited, and may be, for example, 10 to 150 mm, preferably 15 to 90 mm, and more preferably 20 to 70 mm.

A constituent material from which the dilator 40 may be made preferably has flexibility. Examples of the material from which the dilator 40 may be made include thermoplastic polyester elastomer, polyolefin such as polyethylene and polypropylene, polyamide, polyester such as polyethylene terephthalate, fluorinated polymer such as polytetrafluoroethylene (PTFE) and tetrafluoroethylene ethylene copolymer (ETFE), polyether ether ketone (PEEK), polyimide, and the like. Moreover, the dilator 40 may include a material having good visibility for an X-ray contrast material or ultrasound.

The core 50 is a wire rod made of metal that is embedded in the resin material forming the dilator 40 so that the core 50 is positioned between the inner peripheral surface and an outer peripheral surface of the dilator 40. At least one core 50 is provided. In this described and illustrated embodiment, three cores 50 are provided. The plurality of cores 50 are evenly disposed or spaced apart in a circumferential direction of the dilator 40. In the illustrated embodiment disclosed by way of example, the core(s) 51 is completely embedded in the resin forming the elongated body so that an entirety of the outer periphery of the core(s) 50 is covered by the resin. The plurality of cores 50 do not need to be evenly disposed in the circumferential direction of the dilator 40. At least one of the cores 50 is preferably configured to be plastically deformed by being bent so as to allow shaping of the dilator. That is, the core(s) 50 are preferably configured to be deformed (plastically deformed) and to hold the deformed shape. More preferably, all of the cores 50 are configured to be plastically deformed. At least one of the cores 50 preferably has conductivity. The position of a proximal end of the core(s) 50 substantially coincides with the position of the proximal end of the dilator 40. That is, the core(s) 50 may extend to the proximal end of the dilator 40. The position of the proximal end of the core(s) 50 may be different from the position of the proximal end of the dilator 40. For example, the proximal end of the core 50 may be conductive and may be positioned at a proximal side from the proximal end of the dilator 40 (i.e., the conductive core 50 extends proximally beyond the proximal end of the dilator 40) so that the core is easily connected to a conductive wire 35 (see FIG. 2) through which a current is supplied. A position of a distal end of the core(s) 50 substantially coincides with a position a distal end of the shaft part 41. That is, the core(s) 50 may extend to the distal end of the dilator 40. The position of the distal end of the core(s) 50 may be different from the position of the distal end of the shaft part 41. The cores 50 are preferably arranged approximately parallel to the axial center of the dilator 40. The cores 50 do not need to be arranged parallel to the axial center of the dilator 40, and may be disposed in a spiral shape, for example. Moreover, the core(s) 50 may be hollow. The cross-sectional shape of the core(s) 50 may be a perfect circle. The cross-sectional shape of the core(s) 50 is not specially limited, and may be, for example, a rectangle, a square, an ellipse, or the like. In a case where the cross-sectional shape of the core(s) 50 is a rectangle or an ellipse, a long side or a long axis of the cross-section is positioned along the circumferential direction of the dilator 40, and a short side or a short axis of the cross-section is preferably positioned along a radial direction of the dilator 40. Accordingly, it is possible to secure the high flexural rigidity while suppressing the excessive thickness of the dilator 40. The core(s) 50 may have an outer diameter that changes along the axial direction. In a case where the volume occupied by the cores 50 that are arranged in the distal portion of the dilator 40 is large relative to the volume of the dilator 40, the flexural rigidity of the medical device 10 becomes high. Therefore, the medical device 10 easily opens a hole into the biological tissue. In contrast, in a case where the volume occupied by the cores 50 that are arranged in the distal portion of the dilator 40 is small relative to the volume of the dilator 40, the flexural rigidity of the medical device 10 becomes small. Therefore, the biological tissue can be suppressed from being damaged by the medical device 10.

The outer diameter of each core 50 is set as appropriate, and may be, for example, 0.1 to 2.4 mm, preferably 0.1 to 1.3 mm, and more preferably 0.1 to 1.0 mm.

A constituent material from which the core 50 is made is preferably metal that is plastically deformable, and may be, for example, stainless steel, tantalum, titanium, platinum, gold, tungsten, or the like. In a case where a plurality of the cores 50 are present, at least one of the cores 50 may be metal that is plastically deformable, and the remaining cores 50 may be metal that is not so plastically deformable or is at least less plastically deformable than the core made of plastically deformable material. Examples of the metal that is not so plastically deformable include a shape memory alloy such as a Ni—Ti alloy.

The hole formation unit 20 outputs and applies energy for opening a hole in the oval fossa O. The hole formation unit 20 includes an applying unit 21 that is an electrode disposed in the distal portion of the dilator 40, and a conductive unit 22 that conducts current to the applying unit 21. A counter electrode that is an electrode to be paired up with the applying unit 21 is attached to a body surface. The conductive unit 22 is embedded between the inner peripheral surface of the tapered part 42 and the outer peripheral surface of the tapered part 42. The proximal end of the conductive unit 22 is electrically connected to the distal end of the core 50 having the conductivity. A distal end of the conductive unit 22 is electrically connected to the applying unit 21. The conductive unit 22 has a cross-sectional area that decreases toward a distal side or in the distal direction. Therefore, the conductive unit 22 is naturally disposed in the inside of the tapered part 42 the outer diameter of which decreases toward the distal side or in the distal direction.

The proximal end of the conductive unit 22 extends to a proximal end of the tapered part 42. A connection section 23 between the conductive unit 22 and the core 50 is positioned in the proximal end of the tapered part 42. Therefore, after separately forming the shaft part 41 in which the cores 50 are embedded and the tapered part 42 in which the conductive unit 22 is embedded, the shaft part 41 and the tapered part 42 can be joined to each other. In this case, end portions of the cores 50 and an end portion of the conductive unit 22 are positioned at a boundary between the shaft part 41 and the tapered part 42 to be joined to each other, so that the end portions of the cores 50 and the end portion of the conductive unit 22 are aligned to easily form the connection section 23. In a case where the shaft part 41 and the tapered part 42 are formed integrally, and not separately, the end portions of the cores 50 and the end portion of the conductive unit 22 are aligned at a position where the shape of the dilator 40 is changed to easily form the connection section 23. The connection section 23 is embedded in the dilator 40. Therefore, the connection section 23 is not positioned in the lumen 45 of the dilator 40. Accordingly, the guide wire that moves in the lumen 45 can smoothly move, and the connection section 23 does not interfere with that movement. Moreover, the connection section 23 is not positioned outward of the dilator 40. That is, the connection section 23 is not exposed on the outer periphery of the dilator 40. Accordingly, the dilator 40 can smoothly move in the inside of the sheath 60 and the like. The outer diameter of the conductive unit 22 is smaller than the outer diameter of the core 50. Accordingly, the conductive unit 22 is excellently disposed in the inside of the tapered part 42 the outer diameter of which changes, without being bulky. The shape of the conductive unit 22 is not specifically limited. Accordingly, the cross-sectional area of the conductive unit 22 does not need to decrease toward the distal side.

The applying unit 21 to which a high frequency current is supplied via the conductive unit 22 outputs and applies heat to biological tissue to heat biological tissue, thereby modifying the biological tissue and forming a hole in the biological tissue. The applying unit 21 is disposed so as to cover a part of a distal portion of the tapered part 42. That is, the applying unit 21 is exposed on the outer periphery of the distal portion of the tapered part 42. The outer peripheral surfaces of the tapered part 42 and the applying unit 21 are smoothly continuous with each other. This allows the applying unit 21 and the tapered part 42 to smoothly widen a hole to be formed in the biological tissue. The applying unit 21 is disposed on the outer peripheral surface of the tapered part 42 within a range of less than 360 degrees, meaning that the applying unit 21 does not extend around the entire circumference of the tapered part 42 of the elongated body. That is, the applying unit 21 does not have a 360 degree circumferential extent when viewed in cross-section relative to the elongated body. Accordingly, the shape or configuration of the applying unit 21 in a cross-section vertical to (perpendicular to) the axial center of the dilator 40 is C-shaped. Therefore, the applying unit 21 has a concave shape at a side toward the center of the lumen 45 as seen from the distal side. The outer diameter of the outer peripheral surface of the applying unit 21 is smaller than the maximum outer diameter of the tapered part 42 (the outer diameter of the shaft part 41). Therefore, after a small hole has been formed in the oval fossa O by the applying unit 21, the tapered part 42 can expand the hole in the oval fossa O. When a hole to be formed in the oval fossa O is excessively large, the hole remains large after the procedure has been completed, and blood passes through the hole and circulates between the right atrium R and the left atrium L. Therefore, the outer diameter of the applying unit 21 is preferably not excessively large. Moreover, when a hole to be formed in the oval fossa O is excessively small, a resistance when the tapered part 42 expands the hole becomes large, which makes the procedure difficult. Therefore, the outer diameter of the applying unit 21 is preferably not excessively small. The shape of the applying unit 21 in a cross-section vertical to (perpendicular to) the axial center of the dilator 40 does not need to be C-shaped, and may be a circular or polygonal shape, for example.

The length of the applying unit 21 in the axial direction is set as appropriate, and may be, for example, 0.1 to 5.0 mm, preferably 0.1 to 3.0 mm, and more preferably 0.1 to 1.5 mm. The angle at which the applying unit 21 surrounds a central axis of the lumen 45 (i.e., the circumferential extent of the applying unit 21) is not particularly limited, and may be, for example, 1 to 270 degrees, and preferably 45 to 180 degrees. The outer diameter of the applying unit 21 is set as appropriate, and may be, for example, 0.5 to 5.0 mm, preferably 0.5 to 4.0 mm, and more preferably 1.0 to 2.0 mm. The inner diameter of the applying unit 21 is not particularly limited, and is, for example, 0.3 to 4.5 mm, preferably 0.3 to 3.5 mm, and more preferably 0.5 to 1.5 mm. The applying unit 21 does not need to output the high frequency current, but may output, for example, energy such as electromagnetic waves, laser, or cooling, as long as it can modify the biological tissue to form a hole.

A constituent material from which the hole formation unit 20 may be made is not specifically limited as long as it has conductivity. Examples of the material from which the hole formation unit 20 may be made include stainless steel, gold, platinum, tungsten, titanium, or the like.

The operation unit 30 is a part that is gripped and operated by an operator. The operation unit 30 includes a casing 31 that is fixed to the proximal portion of the dilator 40, and a connector 34.

The casing 31 is provided with an instruction portion or bending direction indication potion 32, and a proximal opening portion 33. The instruction portion 32 is positioned in a distal portion of the casing 31, and protrudes to a direction in which the shaft bend 48 bends. The instruction portion 32 is provided to allow the operator to easily recognize a bending direction of the shaft bend 48 that is positioned in the living body, from a protruding direction of the instruction portion 32. A proximal portion of the shaft part 41 is fixed in the inside of the casing 31. The proximal opening portion 33 communicates with the lumen 45 of the dilator 40.

The connector 34 is configured to be connected to an external power supply device (external power supply) that supplies a high frequency current to the hole formation unit 20. The connector 34 includes therein the conductive wire 35. The conductive wire 35 is electrically connected to the cores 50 that extend from the proximal end of the dilator 40. The conductive wire 35 transmits the current that is supplied from the external power supply device to the cores 50.

The sheath 60 provides an access route of a treatment device such as an ablation catheter. The sheath 60 includes a sheath main body 61, a hub 64 that is interlocked with a proximal portion of the sheath main body 61, a port part (port) 66 that communicates with the hub 64, and a valve body 65 in the inside of the hub 64.

The sheath main body 61 is an elongated tubular body in which is accommodated the dilator 40 so that the dilator is axially movable in the sheath main body 61 in the axial direction. The distal portion of the sheath main body 61 includes a sheath bend 62 that is bent at a prescribed angle in the natural state (i.e., in the state in which no force is applied to the sheath main body 61). The sheath bend 62 plays a role in causing the applying unit 21 that is disposed on the dilator 40 having been inserted into the right atrium R to be directed toward the oval fossa O. The distal end of the sheath main body 61 includes a sheath tapered part 63 having an outer diameter that is reduced toward the distal side or in the distal direction in a tapered shape. The dilator 40 is capable of and configured to penetrate or pass through the sheath main body 61. Accordingly, the length of the dilator 40 in the axial direction is longer than the length of the sheath main body 61 in the axis direction.

The hub 64 communicates with a lumen of the sheath main body 61. The port part 66 is interlocked with the hub 64, and communicates with the lumen of the sheath main body 61 through the lumen of the hub 64. The end portion of the port part 66 includes, for example, a three-way stopcock 67. A syringe or the like is connected to the three-way stopcock 67 to allow priming in the lumen of the sheath main body 61, and a contrast agent, a drug, or the like to be injected into the sheath main body 61.

The valve body 65 is a member that seals the hub 64 and the lumen of the sheath main body 61. The valve body 65 is elastically deformable, and includes a through-hole configured to be opened and closed. The valve body 65 slidably comes into contact with the outer peripheral surface of the dilator 40. The valve body 65 suppresses blood from leaking through the sheath 60, and suppresses air from mixing into the body, while allowing the insertion and the extraction of the dilator 40.

In a state where the dilator 40 is inserted into the sheath 60, positions and bending directions of the shaft bend 48 and the sheath bend 62 preferably substantially coincide with each other. This allows the applying unit 21 to direct in a desired direction.

Next, a method of opening a hole in the oval fossa O by using the medical device 10 according to the embodiment described above by way of example, and providing an access route for a device such as an ablation catheter will be described.

First, a needle is punctured into a femoral vein, and a short guide wire is inserted into this needle. Next, the needle is extracted, and a catheter introducer is inserted into a blood vessel along the short guide wire. Next, the shaft bend 48 is bent at the angle β (see FIG. 1), which is any angle desired for the puncture. This shapes the core 50 made of metal at a suitable angle. Therefore, the medical device 10 in a state of being bent can be maintained.

Figure 6A:
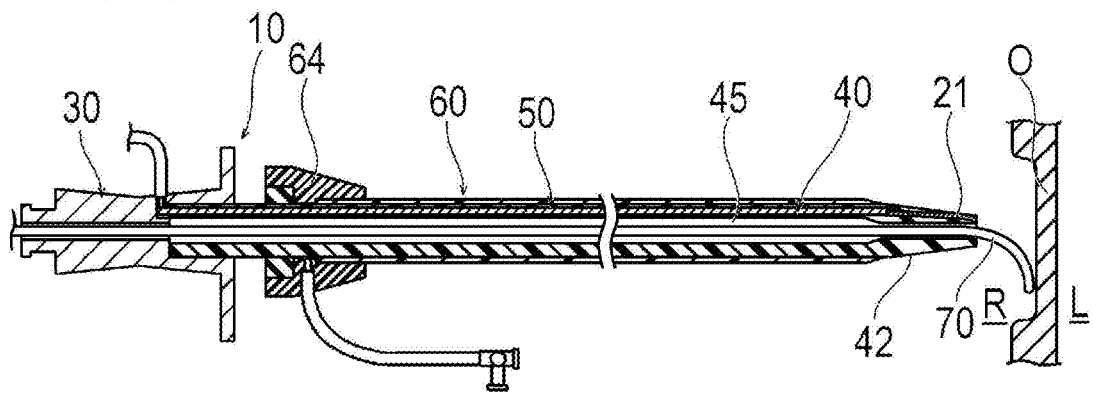
FIGS. 6(A)-6(D) depict cross-sectional views illustrating states when puncture is performed by the medical device.

Next, as illustrated in FIG. 6(A), the dilator 40 is inserted into the inside of the sheath 60 by way of the hub 64. Subsequently, the short guide wire is extracted, and a guide wire 70 is inserted into the catheter introducer. Next, the catheter introducer is extracted while leaving the guide wire 70 in the blood vessel. Next, a proximal end of the guide wire 70 is inserted into the lumen 45 from the distal end of the dilator 40 to insert the medical device 10 into the blood vessel. Next, the medical device 10 is advanced so that a distal portion of the medical device 10 is gradually pushed ahead or moved forward to the right atrium R. Next, the medical device 10 is inserted along the guide wire 70 from the right atrium R in the superior vena cava. Subsequently, when the medical device 10 is pulled back and is led into the right atrium R, as illustrated in FIG. 5 and FIG. 6(A), the distal end of the dilator 40 is automatically guided to the vicinity of the oval fossa O. Thereafter, while an X-ray image is checked, a distal end of the guide wire 70 is led into the inside of the dilator 40. The guide wire 70 may be withdrawn from the dilator 40.

Figure 6B:
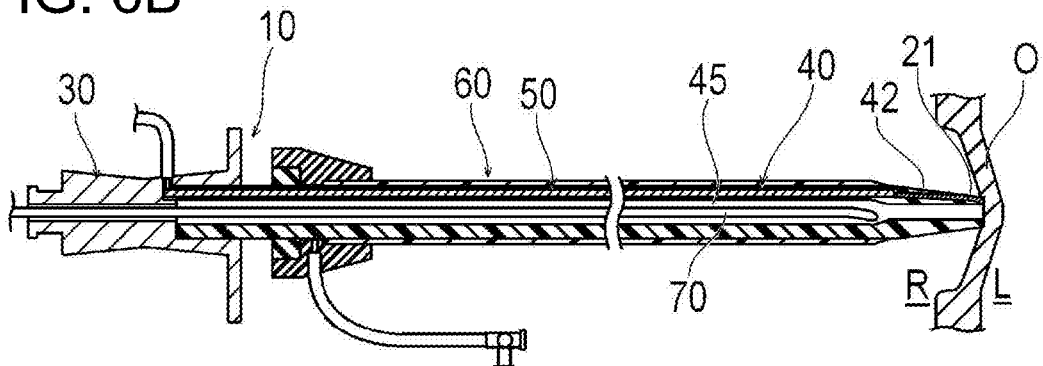

Next, while the insides of the left atrium L and the right atrium R are being observed with an intra cardiac echo catheter (ICE), the medical device 10 is pushed forward or distally toward the distal side. Accordingly, as illustrated in FIG. 6(B), the oval fossa O is pushed toward the left atrium L by the applying unit 21 and the tapered part 42, and the oval fossa becomes a protruded state. In this process, the bend of the distal portion of the dilator 40 is adjusted, so that the distal end of the dilator 40 is easily directed towards the oval fossa O. The oval fossa O does not need to be protruded toward the left atrium L. At the distal end of the dilator 40, a side where the applying unit 21 is provided is positioned at a side of an upper edge portion of the oval fossa O.

Figure 6C:
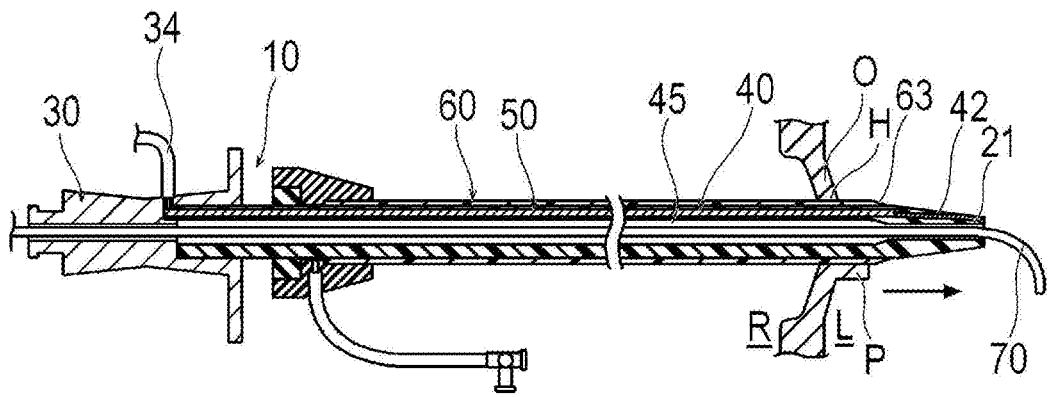
Figure 6D:
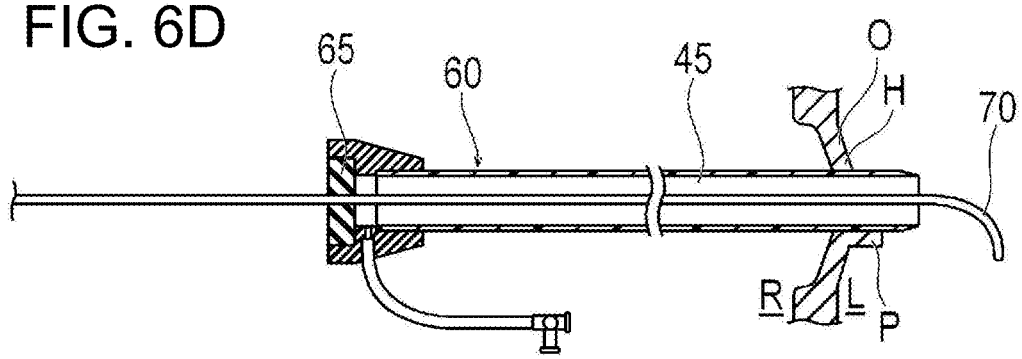
Figure 7:
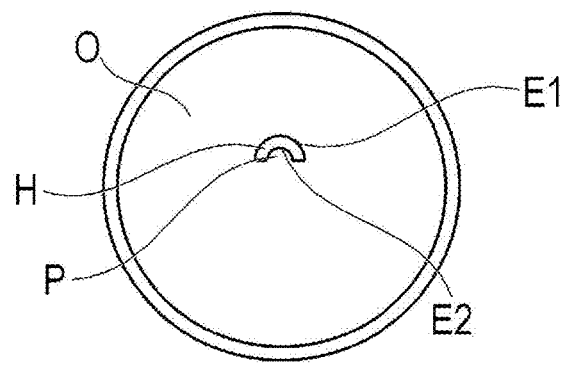
FIG. 7 is a plan view illustrating a hole in the oval fossa formed by the medical device.

Next, the medical device 10 is pushed forward while a high frequency current is supplied to the applying unit 21 from the external power supply device connected to the connector 34. Accordingly, as illustrated in FIG. 6(C) and FIG. 7, biological tissue that is in contact with the applying unit 21 is cauterized, and a hole H in accordance with the C-character shape of the applying unit 21 is formed. That is, as seen in FIG. 7, a C-shaped hole is formed. An outer edge part E1 having a shape corresponding to an outer surface of the applying unit 21, and an inner edge part E2 having a shape corresponding to an inner surface of the applying unit 21 are formed along an edge of the hole H. A site surrounded by the inner edge part E2 of the biological tissue becomes a protrusion P that enters a space formed by ablation. The protrusion P is a part of the fossa ovalis that is not ablated by the applying unit 21. The part is pushed by the medical device when the medical device moves distally. The applying unit 21 is positioned at the side of the upper edge portion of the oval fossa O, and thus easily comes into contact with and cauterizes the biological tissue by being moved forwardly or in the distal direction. After the applying unit 21 penetrates through the oval fossa O and reaches the left atrium L, the supply of the high frequency current to the applying unit 21 may be stopped. If the applying unit surrounding the lumen 45 was configured as a ring-shaped applying unit so that the applying unit extends over 360 degrees, when biological tissue is cauterized or ablated by the applying unit, a part of the biological tissue surrounded by the applying unit would be cut out in a cylindrical shape, and would fall off from the oval fossa O. However, the applying unit 21 in the present embodiment is configured to extend within a range of less than 360 degrees, so that the protrusion P does not fall off from the tissue of the oval fossa O. Therefore, debris that might be carried away by the blood flow is not generated, which results in the high safety. The protrusion P comes into contact with the tapered part 42 (i.e., the tapered part contacts the protrusion P), and is turned over in a direction to be pushed down by the dilator 40. This is generally shown in FIGS. 6(C) and 6(D) where the protrusion is shown being pushed down as the medical device or tapered portion 42 is advanced in the distal direction. Simultaneously, the outer edge part E1 having a shape corresponding to the outer surface of the applying unit 21 comes into contact with the tapered part 42 and widens in the radial direction of the hole, to thus widen the hole.

The applying unit 21 is positioned in the distal portion of the tapered part 42. Therefore, the medical device 10 is further advanced or moved in the forward direction to distally move the tapered part 42 that is positioned at a proximal side of the applying unit 21 into the hole H of the oval fossa O formed by the applying unit 21. Accordingly, the hole H is smoothly expanded. When the medical device 10 is further advanced in the forward or distal direction, the sheath tapered part 63 of the sheath 60 passes through the oval fossa O while expanding the hole H of the oval fossa O, and reaches the left atrium L. The tapered part 42 and the sheath tapered part 63 having diameters reduced toward the distal side (gradually increased toward the proximal direction) allow the hole H in the oval fossa O to be smoothly widened. In this process, the protrusion P of the biological tissue being flexible is pushed to the distal side by the tapered part 42, and deforms to the side of the left atrium L. Therefore, the protrusion P does not prevent the dilator 40 from being inserted into and moved forward relative to the hole H in the oval fossa O.

Next, the guide wire 70 that is positioned in the lumen 45 of the dilator 40 is moved to the distal side or in the distal direction, and to protrude from the dilator 40. Accordingly, a distal portion of the guide wire 70 reaches or is positioned in the left atrium L.

Next, as illustrated in FIG. 6D, the sheath 60 and the guide wire 70 are left or maintained in position, while the dilator 40 is extracted to outside the body. The hole H in the oval fossa O widened by the dilator 40 is maintained by the sheath 60. When the dilator 40 is extracted from the sheath 60, the valve body 65 is closed, so that the leakage of blood and mixing of the air and the like into the blood vessel can be suppressed.

Thereafter, the guide wire 70 is inserted into a target site, and a second medical device such as an ablation device is inserted into the sheath 60 while being advanced along the guide wire 70. The guide wire 70 may be extracted to outside the body before the second medical device is inserted, and the second medical device may be inserted without causing the second medical device to be along the guide wire 70. After the ablation or the like at the target site has been completed, the second medical device is extracted from the sheath 60 to outside the body. In addition, when the sheath 60 is extracted, the hole H in the oval fossa O is contracted. In this process, as illustrated in FIG. 7, the protrusion P (i.e., the portion of the oval fossa O bordered by the part of the biological tissue contacted and cauterized by the applying unit 21) is returned to the hole H in the oval fossa O. Therefore, compared with a case where no protrusion P is formed, a space inside the hole H in which the biological tissue is destroyed becomes smaller. Accordingly, the reproduction of the biological tissue is facilitated. The second medical device to be inserted into the living body through the sheath 60 is not limited to the ablation catheter. The position (target site) at which the second medical device is inserted through the sheath 60 is not limited to the lung vein or the left atrium L, but may be, for example, the left ventricle, the left atrial appendage, the mitral valve, or the like.

The medical device 10 according to the present embodiment is a device for forming a hole in the oval fossa O (biological tissue) in a living body, and includes: the hollow dilator 40 (elongated body) made of resin; at least one core 50 made of metal that is disposed in a part in the circumferential direction of the dilator 40 and extends in the long axis (axial) direction of the dilator 40; and the applying unit 21 that is disposed in the distal portion of the dilator 40 and outputs energy to form the hole in the oval fossa O, in which the core 50 is embedded in between the inner peripheral surface and the outer peripheral surface of the dilator 40, and at least one of the cores 50 has conductivity and is electrically connected to the applying unit 21.

The medical device 10 configured as above has high flexural rigidity because the cores 50 made of metal are disposed in the dilator 40 made of resin, and has high pushing performance necessary for forming a hole in the oval fossa O. Accordingly, for example, even in comparison with a double tube construction in which a tube made of metal is disposed inward of a tube made of resin, the medical device 10 has flexural rigidity equivalent thereto, and has high pushing performance. In addition, the medical device 10 includes the cores 50 made of metal, and thus is capable of being shaped at a desired angle β. Further, the cores 50 made of metal are partially disposed in the circumferential direction of the dilator 40. If the core was configured as a metal tube disposed on the entire circumference of the dilator 40, the core would be likely to become kinked when the dilator 40 bends. In contrast, the cores 50 made of metal according to the embodiment described above by way of example are partially disposed in the circumferential direction of the dilator 40 (i.e., each of the cores 50 extends over less than a 360 degree circumferential extent of the dilator 40), so that a kink can be suppressed from occurring. Thus, the core(s) 50 made of metal have a circumferential extent, when viewed in a cross-section perpendicular to the central axis of the dilator 40, less than 360 degrees as see in FIG. 4. Therefore, an internal space in the lumen 45 of the medical device 10 is appropriately positioned. Accordingly, it is possible to excellently pass the guide wire 70, the contrast agent, and the like through the lumen 45. Moreover, at least one of the cores 50 has conductivity, so that the current can be supplied to the applying unit 21 using the core 50 without separately providing a conductive wire in the medical device 10.

Moreover, the cores 50 are embedded between the inner peripheral surface and the outer peripheral surface of the dilator 40. Accordingly, the cores 50 and the dilator 40 can be integrally deformed. Therefore, the cores 50 can excellently reinforce the dilator 40, and can excellently maintain a bent state of the dilator 40. The cores 50 do not need to be embedded between the inner peripheral surface and the outer peripheral surface of the dilator 40. For example, a part of the cores 50 may be exposed from the inner peripheral surface of the dilator 40 into the lumen 45.

Also, the elongated body is the dilator 40 including the tapered part 42 having the outer diameter that decreases toward the distal side, and the shaft part 41 that is positioned at a proximal side of the tapered part 42 and has an approximately constant outer diameter, in which the lumen 45 that penetrates from the distal end to the proximal end is formed. Accordingly, while forming a hole in the oval fossa O by the applying unit 21 disposed to the dilator 40, it is possible to expand the hole by the tapered part 42. In other words, the dilator 40 that expands the hole in the biological tissue has a puncture function, so that the formation of the hole and the expansion of the hole can be conducted by one instrument as a series of operations, thereby improving the workability.

Additionally, the cores 50 are electrically connected to the applying unit 21 via the conductive unit 22, and the connection section 23 connected with the cores 50 and the conductive unit 22 is positioned in a proximal portion of the tapered part 42. Therefore, the connection section 23 is positioned at the position where the shape of the dilator 40 changes, so that the end portions of the cores 50 and the conductive unit 22 are likely to be aligned.

Moreover, the tapered part 42 and the shaft part 41 are different members, and are joined to each other. Therefore, when the tapered part 42 and the shaft part 41 are joined to each other, end portions of the cores 50 and the conductive unit 22 are aligned to easily form the connection section 23.

Additionally, the cores 50 are arranged approximately parallel to the axial center of the dilator 40. Accordingly, the core 50 has the increased flexural rigidity, and can effectively reinforce the dilator 40.

Moreover, the area of the dilator 40 in a cross-section orthogonal to the axial center of the dilator 40 is larger than the gross area of all the cores 50 in the cross-section. Accordingly, the medical device 10 can increase the flexibility, and reduce a burden to the biological tissue such as a vascular wall to be contacted in the living body.

Also, at least the two cores 50 are provided, and are evenly disposed (equally spaced apart) in the circumferential direction of the dilator 40. Accordingly, the flexural rigidity of the medical device 10 becomes approximately uniform without depending on the direction of bending. Therefore, the operability of the medical device 10 is improved.

Further, the core 50 may be solid. Accordingly, the medical device 10 has the increased flexural rigidity, and can obtain a high pushing performance. Moreover, the core 50 is solid, and thus can suppress a kink of the core 50.

The disclosure is not limited to the above-described embodiment, but various changes by those skilled in the art can be made within the technical scope of this disclosure. For example, a biological tissue in which a hole is formed by the medical device 10 does not need to be the oval fossa O.

Moreover, the elongated body to which the applying unit is disposed does not need to be a dilator that expands the hole in the biological tissue. For example, the elongated body to which the applying unit is disposed may be a transseptal needle that is inserted into the dilator. In this case, the outer diameter of the transseptal needle serving as a medical device to which the applying unit is disposed is smaller than the outer diameter of the dilator.

Figure 8A:
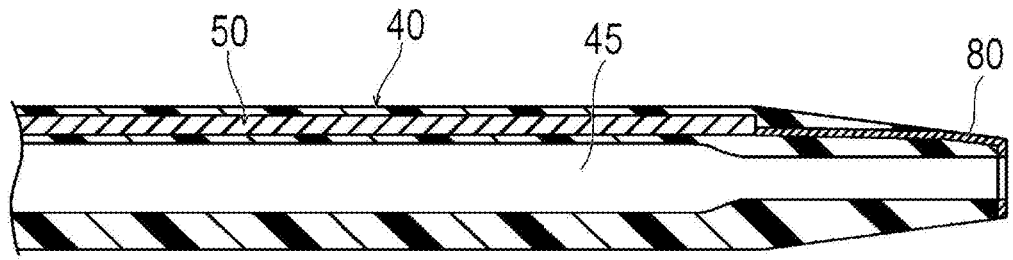
FIGS. 8(A) and 8(B) depict cross-sectional views illustrating modification examples of the medical device.

Also, as in a first modification example illustrated in FIG. 8(A), an output unit 80 may be provided at the tapered part 42 over 360 degrees. The output unit 80 includes a through-hole as shown in FIG. 8(A). Features that are the same or similar to those described above are identified by the same reference numerals and a detailed description of such features is not repeated.

Figure 8B:
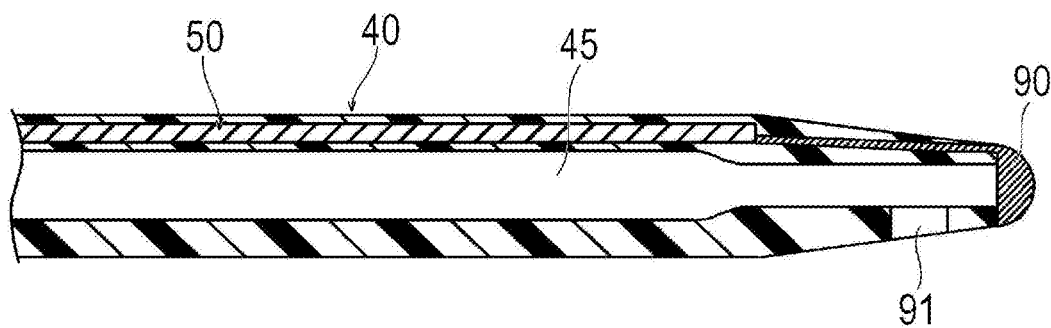

According to a second modification example illustrated in FIG. 8(B), an applying unit 90 does not need to be provided with a through-hole that is communicated with the lumen 45 of the tapered part 42. Instead, the shaft part 41 may preferably be provided with a side hole 91 in which the lumen 45 is opened, in a distal portion thereof. Accordingly, it is possible to inject a contrast agent or a drug via the side hole 91, and detect a pressure.

Moreover, the applying unit may be one of two electrodes included in a bipolar electrode. In this case, the counter electrode plate that is paired up with the applying unit is disposed in any place in the dilator 40 that comes into contact with the biological tissue. The exposed electrode area of the counter electrode plate is larger than the area of the applying unit.

The detailed description above describes embodiments of a medical device and method for forming a hole in biological tissue in a living body representing examples of the inventive medical device and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for forming a hole in biological tissue in a living body, the medical device comprising:
    a hollow elongated body made of resin and possessing a center axis, the hollow elongated body possessing a distal portion and a proximal portion that are spaced apart in an axial direction of the hollow elongated body, the hollow elongated body possessing an outer peripheral surface and an inner peripheral surface, the outer peripheral surface of the distal portion of the hollow elongated body being tapered and terminating at an axial end face at a distal-most end of the hollow elongated body so that an outer diameter of the distal portion of the hollow elongated body decreases toward the distal-most end of the hollow elongated body;
    a core made of metal that extends in the axial direction of the hollow elongated body, the core made of metal having a circumferential extent less than 360 degrees as seen in a cross-section perpendicular to the center axis of the hollow elongated body, the core having a distal end that possesses an outer diameter;
    an applying unit that is disposed at the distal portion of the hollow elongated body and that applies energy to the biological tissue to form the hole in the biological tissue, the outer peripheral surface of the distal portion of the hollow elongated body that is tapered extending proximally beyond the applying unit;
    the core being embedded between the inner peripheral surface of the hollow elongated body and the outer peripheral surface of the hollow elongated body; and
    the core is a conductive core and is electrically connected to the applying unit by a conductive unit; and
    the conductive unit having an outer diameter smaller than the outer diameter of the distal end of the core.

2. The medical device according to claim 1, wherein the hollow elongated body is a dilator that includes a proximal end and a distal end, the distal portion of the hollow elongated body constituting a tapered part of the dilator located at the distal portion of the hollow elongated body, the dilator including a shaft part positioned proximal of the tapered part and possessing an approximately constant outer diameter, the dilator also including a lumen that extends from the distal-most end of the hollow elongated body to the proximal end of the dilator.

3. The medical device according to claim 2, wherein a connection section connected with the core and the conductive unit is positioned in a proximal portion of the tapered part of the hollow elongated body.

4. The medical device according to claim 2, wherein the tapered part and the shaft part are fabricated separate from one another and are joined to each other after being separately formed.

5. The medical device according to claim 1, wherein the core is disposed approximately parallel to the center axis of the elongated body.

6. The medical device according to claim 1, wherein the core is a first core, and further comprising at least one additional core made of metal, extending in the axial direction of the hollow elongated body and having a circumferential extent less than 360 degrees a cross-sectional area of the hollow elongated body orthogonal to the center axis of the hollow elongated body is larger than a total cross-sectional area of all the cores.

7. The medical device according to claim 1, wherein the core is a first core, and further comprising a second core, the first and second cores being evenly disposed in a circumferential direction of the hollow elongated body as seen in the cross-section perpendicular to the center axis of the hollow elongated body.

8. The medical device according to claim 1, wherein the core is solid.

9. The medical device according to claim 1, wherein the core is a first core, and further comprising a plurality of additional cores, the first core and the additional cores being circumferentially spaced apart from one another as seen in the cross-section perpendicular to the center axis of the hollow elongated body, at least one of the first core and the additional cores being made of a plastically deformable metal.

10. The medical device according to claim 9, the first core and the additional cores are parallel to one another.

11. The medical device according to claim 9, wherein a total cross-sectional area of the first core and all of the additional cores orthogonal to respective center axes of the first core and all of the additional cores is less than a cross-sectional area of the hollow elongated body orthogonal to the center axis of the hollow elongated body.

12. The medical device according to claim 9, wherein the first core and the additional cores are equally spaced apart from one another in a circumferential direction of the hollow elongated body as seen in the cross-section perpendicular to the central axis of the hollow elongated body.

13. A medical device for forming a hole in biological tissue in a living body, the medical device comprising:
- an elongated body made of resin and possessing a center axis, the elongated body possessing an outer peripheral surface, the elongated body possessing a distal portion and a proximal portion that are spaced apart in an axial direction of the elongated body, the distal portion of the elongated body terminating at a distal end of the elongated body and the proximal portion of the elongated body terminating at a proximal end of the elongated body, the outer peripheral surface of the distal portion of the elongated body being tapered and terminating at an axial end face at the distal end of the elongated body so that an outer diameter of the distal portion of the elongated body decreases in a direction toward the distal end of the elongated body, the elongated body including a lumen that extends between the proximal and distal portions of the elongated body, the lumen communicating outside the elongated body at both the proximal portion of the elongated body and the distal portion of the elongated body, the lumen in the elongated body being surrounded by an inner peripheral surface of the elongated body;
- a core configured to be connected to an external power supply that supplies current, the core being made of a conductive metal that conducts the current supplied by the external power supply device when the core is connected to the external power supply and that is plastically deformable when bent so that when the elongated body is bent into a bent shape the core holds the bent shape of the elongated body, the core being completely embedded in the resin from which the elongated body is made so that an entirety of the outer periphery of the core is covered by the resin from which the elongated body is made, the core extending in the axial direction of the elongated body between the proximal portion of the elongated body and the distal portion of the elongated body, the core made of metal having a circumferential extent, when viewed in a cross-section perpendicular to the center axis of the elongated body, that is less than 360 degrees; and
- an electrode positioned at the distal portion of the elongated body, the electrode possessing an outer surface that is exposed so that the outer surface of the electrode is contactable with the biological tissue in the living body, the electrode being electrically connected to the core so that current conducted by the core when the core is connected to the external power supply is supplied to the electrode to form the hole in the biological tissue in the living body, the outer peripheral surface of the distal portion of the elongated body that is tapered extending proximally beyond the electrode.

14. The medical device according to claim 13, wherein the core is a first core, further comprising a second core made of a metal that is plastically deformable when the second core is bent so that when the elongated body is bent into the bent shape the second core holds the bent shape of the elongated body the second core being circumferentially spaced from the first core as seen in the cross-section perpendicular to the center axis of the hollow elongated body.

15. The medical device according to claim 13, wherein the outer peripheral surface of the distal portion of the elongated body gradually tapers.

16. The medical device according to claim 13, wherein the core is one of a plurality of cores, all of the cores being parallel to one another and being embedded in the resin from which the elongated body is made, the cores being circumferentially spaced apart from one another as seen in the cross-section perpendicular to the center axis of the hollow elongated body.

17. The medical device according to claim 13, wherein the core is one of a plurality of cores, all of the cores being parallel to one another and being equally spaced apart from each other in a circumferential direction of the elongated body as seen in the cross-section perpendicular to the center axis of the hollow elongated body.

18. The medical device according to claim 13, wherein a distal end of the elongated body is closed, and the distal portion of the elongated body including a side hole communicating the lumen in the elongated body to outside the elongated body at the distal portion of the elongated body.

19. A method comprising:
- introducing a portion of a medical device into a living body, the medical device comprising: a hollow elongated body made of resin and possessing distal and proximal portions that are spaced apart in an axial direction of the hollow elongated body, the hollow elongated body possessing a center axis and an outer peripheral surface, the outer peripheral surface of the distal portion of the hollow elongated body being tapered and terminating at an axial end face at a distal-most end of the hollow elongated body so that an outer diameter of the distal portion of the hollow elongated body decreases toward the distal-most end of the hollow elongated body; a core made of conductive metal, the core being plastically deformable when bent, the core extending in the axial direction of the hollow elongated body and being embedded in the resin from which the hollow elongated body is made, the core made of metal having a circumferential extent less than 360 degrees relative to the hollow elongated body as seen in the cross-section perpendicular to the central axis of the hollow elongated body; and an electrode disposed at the distal portion of the hollow elongated body and electrically connected to the core, the outer peripheral surface of the distal portion of the hollow elongated body that is tapered extending proximally beyond the electrode;
- bending the hollow elongated body into a bent shape to plastically deform the core so that the core holds the bent shape of the hollow elongated body, the bending of the hollow elongated body into the bent shape occurring before the introducing of the portion of the medical device into the living body;

moving the electrode at the distal portion of the hollow elongated body into contact with biological tissue in the living body;

applying energy to the core made of the conductive metal so that the energy is conducted to the electrode; and the energy supplied to the electrode and the contact of the electrode with the biological tissue in the living body causing the biological tissue that is in contact with the electrode to cauterize the biological tissue in the living body and produce a through hole in the biological tissue in the living body.

20. The method according to claim 19, the method further comprising moving the hollow elongated body forward after forming the through hole in the biological tissue in the living body so that the tapered outer peripheral surface of the distal portion of the hollow elongated body gradually widens the through hole in the biological tissue in the living body.

21. A medical device for forming a hole in biological tissue in a living body, the medical device comprising:

a hollow elongated body made of resin and possessing a center axis, the hollow elongated body possessing a distal portion and a proximal portion that are spaced apart in an axial direction of the hollow elongated body, the hollow elongated body possessing an outer peripheral surface and an inner peripheral surface, the outer peripheral surface of the distal portion of the hollow elongated body being tapered and terminating at an axial end face at a distal-most end of the hollow elongated body so that an outer diameter of the distal portion of the hollow elongated body decreases toward the distal-most end of the hollow elongated body;

a first core made of metal that extends in the axial direction of the hollow elongated body, the first core made of metal having a circumferential extent less than 360 degrees as seen in a cross-section perpendicular to the center axis of the hollow elongated body;

an applying unit that is disposed at the distal portion of the hollow elongated body and that applies energy to the biological tissue to form the hole in the biological tissue, the outer peripheral surface of the distal portion of the hollow elongated body that is tapered extending proximally beyond the applying unit;

the first core being embedded between the inner peripheral surface of the hollow elongated body and the outer peripheral surface of the hollow elongated body;

the first core is a conductive core and is electrically connected to the applying unit; and a second core made of metal that extends in the axial direction of the hollow elongated body, the second core made of metal having a circumferential extent less than 360 degrees as seen in the cross-section perpendicular to the center axis of the hollow elongated body, the second core being spaced from the first core and being embedded in the resin of the hollow elongated body.

* * * * *